(12) United States Patent
Terada

(10) Patent No.: US 7,947,258 B2
(45) Date of Patent: May 24, 2011

(54) AQUEOUS HAIR CLEANSING AGENT (75) Inventor: Eiji Terada, Sumida-ku (JP)

(73) Assignee: Kao Corporation, Tokyo (JP)

( * ) Notice: Subject to any disclaimer, the term of this patent is extended or adjusted under 35 U.S.C. 154(b) by 343 days.

(21) Appl. No.: 11/751,256

(22) Filed: May 21, 2007

(65) Prior Publication Data

US 2007/0269398 A1    Nov. 22, 2007

(30) Foreign Application Priority Data

May 22, 2006    (JP) .................................. 2006-141430

(51) Int. Cl.
*A61K 8/89* (2006.01)
*A61K 8/73* (2006.01)

(52) U.S. Cl. .................. 424/70.122; 424/70.13

(58) Field of Classification Search ............... 424/70.212
See application file for complete search history.

(56) References Cited

U.S. PATENT DOCUMENTS

| | | | |
|---|---|---|---|
| 5,085,857 A | 2/1992 | Reid et al. | |
| 2003/0147822 A1* | 8/2003 | Doi et al. | 424/70.1 |
| 2005/0075497 A1* | 4/2005 | Utz et al. | 536/114 |
| 2005/0255074 A1* | 11/2005 | Hanada et al. | 424/70.122 |
| 2006/0051308 A1 | 3/2006 | Terada | |
| 2006/0154835 A1 | 7/2006 | Terada | |

FOREIGN PATENT DOCUMENTS

| | | |
|---|---|---|
| EP | 1 226 814 A1 | 7/2002 |
| EP | 1 428 499 A2 | 6/2004 |
| EP | 1 739 095 A1 | 1/2007 |
| JP | 2003-327603 | 11/2003 |
| JP | 2004-67640 | 3/2004 |
| JP | 2004-203801 | 7/2004 |
| JP | 2005-272658 | 10/2005 |
| WO | WO/2004/014326 * | 8/2003 |
| WO | WO 2006/052580 | 5/2006 |

OTHER PUBLICATIONS

U.S. Appl. No. 11/751,217, filed May 21, 2007, Terada.
U.S. Appl. No. 11/313,740, filed Dec. 22, 2005, Terada.

* cited by examiner

*Primary Examiner* — Shanon A Foley
*Assistant Examiner* — Sarah Al-Awadi
(74) *Attorney, Agent, or Firm* — Oblon, Spivak, McClelland, Maier & Neustadt, L.L.P.

(57) ABSTRACT

An aqueous hair cleansing agent containing the following components (A), (B) and (C):
 (A): an anionic surfactant;
 (B): a cationized tara gum; and
 (C): an amino-modified silicone represented by a specific formula.

13 Claims, 2 Drawing Sheets

AQUEOUS HAIR CLEANSING AGENT

FIELD OF THE INVENTION

The present invention relates to an aqueous hair cleansing agent.

BACKGROUND OF THE INVENTION

Water soluble cationized polymers such as cationized cellulose and cationized guar gum have been conventionally used for hair cleansing agents in order to provide the hair with conditioning effects. Cationized polymers in hair cleansing agents are thought to provide the hair with conditioning effects by easily remaining on the hair surface as a water insoluble complex formed with an anionic surfactant when they are diluted with water. They are however not so effective for the hair damaged by chemical treatment with a hair coloring agent, permanent wave agent or the like, and a phenomenon of tangling or friction between individual hairs still occurs while the agent is rinsed off.

In order to improve the conditioning effects, proposed is the use of a cationized tara gum obtained by cationizing a polysaccharide available from the endosperm of the seeds of tara (scientific name: *Caesal pinia Spinosa*) that is a leguminous plant (JP-A-2004-203801). It is also proposed to use a cationized tara gum in combination with cationized guar gum in a hair cleansing agent (JP-A-2005-272658). However, the conditioning effects on the damaged hair are still insufficient.

Amino-modified silicones are sometimes added to hair cleansing agents in order to improve the conditioning effects. A hair cleansing agent containing an amino-modified or ammonium-modified silicone having a high molecular weight is described In JP-A-5-85918. The amino-modified silicone or the like described therein has, in a side chain of the polysiloxane backbone thereof, an alkylene amine or alkylene ammonium salt so that the agent has a high hydrophobic property and as a result, has problems in the stability because of poor solubility or dispersibility in the hair cleansing agent. In addition, it reduces the foaming of the hair cleansing agent and the hair becomes tough or greasy at the time of rinsing off of the agent.

SUMMARY OF THE INVENTION

The present invention provides an aqueous hair cleansing agent comprising the following components (A), (B) and (C):
 (A) an anionic surfactant,
 (B) a cationized tara gum, and
 (C) an amino-modified silicone represented by the formula (1) or (4):

wherein,
$R^1$ each independently represents a monovalent hydrocarbon group, a hydroxy group or an alkoxy group,
$R^2$ each independently represents a monovalent hydrocarbon group,
$R^3$ represents a divalent $C_{1-10}$ hydrocarbon group,
$R^4$ represents a group represented by the formula (2) or (3):

wherein Y represents a hydrogen atom or a group —$CH_2$—$CH(OH)$—$R^3$—OH, $R^3$ having the same meaning as described above, $R^5$ represents a hydrogen atom or a group —$R^3NY_2$, Y and $R^3$ having the same meanings as described above, with the proviso that all the Ys do not represent a hydrogen atom at the same time, a in formula (1) stands for a number from 25 to 1000, and b stands for a number from 1 to 200;

wherein, $R^6$ each independently represents a hydrogen atom or a monovalent $C_{1-6}$ hydrocarbon atom, $R^7$ represents either $R^6$ or E, E represents a group represented by —$R^8$—Z, wherein $R^8$ represents a direct bond or a divalent $C_{1-20}$ hydrocarbon group, and Z represents a primary, secondary or tertiary amino-containing group or ammonium-containing group, X represents a divalent group, c stands for a number of 2 or greater, d stands for a number of 1 or greater, n stands for a number from 2 to 10, e stands for a number of 4 or greater and f stands for a number of 2 or greater.

BRIEF DESCRIPTION OF THE DRAWINGS

FIG. 2(*a*) is a top view of a disk to which hairs are to be implanted and FIG. 2(*b*) is a cross-sectional view of a disk to which the hairs have been implanted.
 1: Hair
 10: Container
 11: Disk
 20: Lid
 21: First protrusion
 22: Second protrusion
 23: Foam inducing wall
 24: Hair-entrapping-prevention pin
 25: Inlet
 30: Motor
 40: Control unit
 41: Support
 50: Metering instrument
 51: Water inlet
 60: Torque detector
 P: Implant hole

DETAILED DESCRIPTION OF THE INVENTION

The present invention relates to an aqueous hair cleansing agent which provides, even if used for the hair damaged by chemical treatment, rapid foaming and smooth feeling of foam during shampooing, provides smooth feel to the hair during rinsing, provides the finished hair with luster and manageability, and has excellent storage stability.

The present inventor has found out an aqueous hair cleansing agent which is excellent in the performance and feel of foam, and finish, even if it is applied to the damaged hair, and also is excellent in storage stability by using, in combination, an anionic surfactant, a cationized tara gum and an amino-modified silicone having a specific structure.

As the anionic surfactant (A), sulfate-, sulfonate- and carboxylate-based surfactants are usable. Specific examples include alkyl sulfates, alkenyl sulfates, polyoxyalkylene alkyl ether sulfates, polyoxyalkylene alkenyl ether sulfates, alkyl sulfosuccinates, polyoxyalkylene alkyl sulfosuccinates, alkane sulfonates, higher fatty acid salts, and alkyl ether carboxylates. Of these, polyoxyalkylene alkyl ether sulfates, polyoxyalkylene alkenyl ether sulfates, alkyl sulfates, and alkenyl sulfates are preferred, with those represented by the following formula (5) or (6) being more preferred:

$$R^9O(CH_2CH_2O)_mSO_3M \quad (5)$$

$$R^9OSO_3M \quad (6)$$

wherein, $R^9$ represents a $C_{10-18}$ alkyl or alkenyl group, M represents an alkali metal, alkaline earth metal, ammonium, a cation derived from alkanolamine or basic amino acid, and m stands for an average number by weight of from 1 to 5.

Of these, polyoxyethylene alkyl ether sulfates of the formula (5) in which $R^9$ represents a $C_{12-14}$ alkyl group, m stands for a number of 1 on weight average and M represents ammonium or sodium are preferred because they can satisfy both speedy foaming and good feel of foam.

As Component (A), the above-described anionic surfactants may be used either singly or in combination of two or more. The content of it in the aqueous hair cleansing agent of the present invention preferably ranges from 1 to 30 weight %, more preferably from 5 to 25 weight %, still more preferably from 8 to 20 weight % from the viewpoints of foaming property, liquid state during use and cleansing property.

Component (B) of the present invention is a cationized tara gum. Tara gum which is an origin of the cationized tara gum is obtained from the endosperm of the seeds of tara (scientific name: *Caesalpinia Spinosa*) belonging to leguminous plants and is a galactomannan polysaccharide composed of a main chain of mannose units and a side chain of galactose attached thereto. The ratio of mannose to galactose in tara gum is 3:1.

In the cationized tara gum to be used in the present invention, some hydroxyl groups contained in the galactomannan structure in the tara gum have been substituted with a quaternary nitrogen-containing group. More in detail, it can be prepared by reacting tara gum with a compound having a quarternary nitrogen-containing group such as glycidyl trialkylammonium salt or 3-halogeno-2-hydroxypropyltrialkylammonium salt. This reaction is effected in the presence of an alkali in a proper solvent, preferably a hydrous alcohol. The quaternary nitrogen-containing group can be introduced into the tara gum in accordance with the conventionally known process.

Although no particular limitation is imposed on the cationization degree of cationized tara gum, that is the average number of moles of the quaternary nitrogen-containing group to be added per monosaccharide unit, it is preferably from 0.1 to 0.5. When the cationization degree is less than 0.1, satisfactory conditioning effects cannot be recognized owing to an insufficient adsorption amount to the hair. The cationization degree exceeding 0.5, on the other hand, causes a sticky feel during use and at the same time, worsens the foaming property.

Examples of commercially available products include "Catinal CTR-100" and "Catinal CTR-200" (each, product of Toho Chemical Industry).

As Component (B), these cationized tara gums can be used either singly or in combination of two or more. The content of Component (B) in the aqueous hair cleansing agent of the present invention is preferably from 0.01 to 10 weight %, more preferably from 0.02 to 5 weight %, even more preferably from 0.03 to 2 weight % from the standpoints of decreasing the friction between individual hairs during rinsing.

Component (C) is an amino-modified silicone represented by the formula (1) or (4):

wherein,
$R^1$ each independently represents a monovalent hydrocarbon group, a hydroxy group or an alkoxy group,
$R^2$ each independently represents a monovalent hydrocarbon group,
$R^3$ represents a divalent $C_{1-10}$ hydrocarbon group,
$R^4$ represents a group represented by the formula (2) or (3):

wherein Y represents a hydrogen atom or a group —$CH_2$—$CH(OH)$—$R^3$—OH, $R^3$ having the same meaning as described above, $R^5$ represents a hydrogen atom or a group —$R^3NY_2$, Y and $R^3$ having the same meanings as described above, with the proviso that all the Ys do not represent a hydrogen atom at the same time, a in the formula (1) stands for a number from 25 to 1000, and b stands for a number from 1 to 200;

wherein, $R^6$ each independently represents a hydrogen atom or a monovalent $C_{1-6}$ hydrocarbon group, $R^7$ represents either $R^6$ or E, E represents a group represented by —$R^8$—Z, wherein $R^8$ represents a direct bond or a divalent $C_{1-20}$ hydrocarbon group, and Z represents a primary, secondary or tertiary amino-containing group or ammonium-containing group, X represents a divalent group, c stands for a number of 2 or greater, d stands for a number of 1 or greater, n stands for a number from 2 to 10, e stands for a number of 4 or greater and f stands for a number of 2 or greater.

The amino-modified silicone represented by the formula (1) is an amino-modified silicone having, in a side chain thereof, a specific amino functional group.

In the formula (1), examples of the monovalent hydrocarbon group as $R^1$ include alkyl groups and aryl groups. As $R^1$, $C_{1-3}$ alkyl (especially, methyl) groups and $C_{1-15}$, especially $C_{10-15}$ alkoxy groups are preferred.

Preferred examples of the monovalent hydrocarbon group as $R^2$ include $C_{1-6}$ alkyl groups such as methyl, ethyl, propyl, butyl, pentyl and hexyl, $C_{6-10}$ aryl groups such as phenyl, tolyl and xylyl, and $C_{6-10}$ aralkyl groups such as benzyl and phenethyl. Of these, alkyl groups are preferred, with a methyl group being more preferred.

Examples of the divalent $C_{1-10}$ hydrocarbon group as $R^3$ include alkylene groups such as methylene, ethylene, trimethylene, propylene, tetramethylene, methyltrimethylene, ethylethylene and dimethylethylene; and alkylene-arylene groups represented by the formula $-(CH_2)_2-C_6H_4-$. Of these, $C_{2-4}$ alkylene groups are preferred.

The group $-CH_2-CH(OH)-R^3-OH$ as Y is preferably a 2,3-dihydroxypropyl group.

As $R^4$, groups represented by the formula (3) are preferred, while as $R^5$ in the formula (3), 2-N-(2,3-dihydroxypropyl)aminoethyl group and 2-N,N-bis(2,3-dihydroxypropyl)aminoethyl group are preferred.

In the formula (1), the number a is preferably from 50 to 400, and the number b is preferably from 1 to 20.

The amino-modified silicone represented by the formula (1) can be synthesized, for example, by reacting an amino-modified silicone with an epoxy-functional compound such as glycidol as described in EP0399706A2. Examples of the amino-modified silicone represented by the formula (1) include compounds represented by the below-described formula:

wherein, $R^{10}$ represents a $C_{13-15}$ alkyl group and from 70 to 80% of Y's represent a group $-CH_2CH(OH)CH_2OH$ and from 30 to 20% of them represent a hydrogen atom, and "8500 Conditioning Agent" of Dow Corning (CAS No. 237753-63-8) can be given as one example of a commercially available product.

The amino-modified silicone represented by the formula (4) is a block copolymer composed of a polyoxyalkylene block and an amino-modified polysiloxane block having, in a side chain thereof, an amino functional group.

In the formula (4), $R^6$ each independently represents preferably a hydrogen atom, a $C_{1-6}$ alkyl group or a phenyl group, with methyl and ethyl groups being more preferred and methyl group being even more preferred.

Examples of the divalent $C_{1-20}$ hydrocarbon group as $R^8$ include methylene, ethylene, propylene, butylene, pentylene, hexylene, heptylene, octylene, decylene and octadecylene groups. Of these, methylene, ethylene and propylene groups are more preferred.

As Z, an amino-containing group or ammonium-containing group represented by the formula (7) or (8) is preferred:

wherein, $R^{11}$ represents $R^{12}$ each represents a hydrogen atom or a monovalent hydrocarbon group and these $R^{12}$s may be the same or different, g and h each stands for an integer of from 0 to 6 and $T^-$ represents a halide ion or an organic anion.

Examples of the monovalent hydrocarbon group represented by $R^{12}$ in the formulas (7) and (8) include methyl, ethyl and propyl groups. Specific examples of $T^-$ include halide ions such as chloride ions, iodide ions, and bromide ions, and organic anions such as methosulfate, ethosulfate, methophosphate and ethophosphate.

In the formula (4), the group E is preferably $-(CH_2)_3-NH_2$, $-(CH_2)_3-N(CH_3)_2$, $-(CH_2)_3-NH-(CH_2)_2-NH_2$, $-(CH_2)_2-NH-(CH_2)_2-N(CH_3)_2$, or $-(CH_2)_3-N^+(CH_3)_3Cl^-$, more preferably $-(CH_2)_3-NH-(CH_2)_2-NH_2$.

In the formula (4), preferred examples of the divalent group represented by X include alkylene groups and arylene groups, more specifically, ethylene, propylene, trimethylene, tetramethylene and isobutylene groups, with tetramethylene and isobutylene groups being more preferred.

In the formula (4), c stands for the number from 2 to 1000, d stands for the number from 1 to 50, e stands for the number from 4 to 200, and f stands for the number of from 2 to 100.

In the block copolymer represented by the formula (4), a percentage of the siloxane block is preferably from 25 to 97 weight %, more preferably from 35 to 90 weight %, even more preferably from 50 to 80 weight % of the whole copolymer.

The block copolymer has preferably at least an average molecular weight of 1200. The average molecular weight as used herein is determined in the conventional manner by using GPC while using chloroform as an eluent and polystyrene as a standard substance.

The term "siloxane block" as used herein means a siloxane having two $R^6$ groups, each represented by $-[Si(R^6)_2-O]-$ and the term "percentage of the siloxane block" means a ratio, in terms of weight %, of the molecular weight of the siloxane block to that of the block copolymer (4). The percentage within the above-described range is preferred because the block copolymer (4) shows high solubility or dispersibility in an aqueous hair cleansing agent and in addition, remains well on the hair.

Of the amino-modified silicones represented by the formula (4), amino-modified polysiloxane-polyoxyalkylene block copolymers having a polymerization unit represented by the formula (9) are more preferred:

wherein, c, d and f have the same meanings as described above, i stands for a number of 4 or greater and j stands for a number from 0 to 30.

In the formula (9), c, d, i and f stand for preferably a number from 2 to 1000, a number from 1 to 50, a number from 4 to 200 and a number from 2 to 100, respectively. In the above formula, —O($C_2H_4O$)$_i$($C_3H_6O$)$_j$ unit may be either block or random.

Examples include "FZ-3789", "DOW CORNING TORAY SS-3588", and "DOW CORNING TORAY SILSTYLE104", each product of Dow Corning Toray.

These amino-modified silicones as Component (C) may be used either singly or in combination of two or more. The content of Component (C) in the aqueous hair cleansing agent of the present invention is preferably from 0.01 to 10 weight %, more preferably from 0.02 to 5 weight %, even more preferably from 0.03 to 2 weight % from the standpoint of decreasing friction between individual hairs during rinsing.

A weight ratio of the Components (B)/(C) is preferably from 1/10 to 10/1, more preferably from 1/5 to 5/1 from the standpoint of smoothness during foaming and rinsing.

The aqueous hair cleansing agent of the present invention may contain a nonionic surfactant or amphoteric surfactant in order to improve the cleansing performance further.

Examples of the nonionic surfactant include polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglyceryl alkyl ethers, polyglyceryl fatty acid esters, fatty acid alkanolamides, alkyl glycosides, monoalkyl glyceryl ethers, and monoalkenyl glyceryl ethers.

Of these, polyoxyalkylene sorbitan fatty acid esters such as polyoxyethylene sorbitan fatty acid esters, polyoxyalkylene fatty acid esters such as polyoxyalkylene ($C_8$-$C_{20}$) fatty acid esters, polyoxyalkylene (hydrogenated) castor oils such as polyoxyethylene hydrogenated castor oil, and alkyl glycosides are preferred.

The fatty acid alkanolamides are also preferred. They may be either monoalkanolamides or dialkanolamides. They have preferably a $C_{8-18}$, more preferably $C_{10-16}$ acyl group. Those having a $C_{2-3}$ hydroxyalkyl group are also preferred. Examples include oleic acid diethanolamide, palm kernel oil fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide, and lauric acid monoethanolamide.

As Component (D), monoalkyl glyceryl ethers and monoalkenyl glyceryl ethers are also preferred. As the alkyl or alkenyl group of them, $C_{4-10}$ alkyl or alkenyl groups are preferred, with linear or branched $C_{8-10}$ alkyl or alkenyl groups being more preferred. Specific examples include n-butyl, isobutyl, n-pentyl, 2-methylbutyl, isopentyl, n-hexyl, isohexyl, n-heptyl, n-octyl, 2-ethylhexyl, n-decyl and isodecyl groups. Of these, 2-ethylhexyl and isodecyl groups are more preferred.

Examples of the amphoteric surfactant include betaine surfactants. Of these, alkyldimethylaminoacetic acid betaines, fatty acid amidopropylbetaines and alkylhydroxysulfobetaines are more preferred, of which fatty acid amidopropylbetaines are even more preferred. The fatty acid amidopropylbetaines have preferably a $C_{8-18}$, more preferably $C_{10-16}$ acyl group. Lauric acid amidopropylbetaine, palm kernel oil fatty acid amidopropylbetaine and coconut oil fatty acid amidopropylbetaine are even more preferred.

In the aqueous hair cleansing agent, these nonionic or amphoteric surfactants may be used either singly or in combination of two or more. In order to provide a preferred aqueous hair cleansing agent of the present invention in the form of an aqueous liquid cleansing agent, use of a fatty acid amidopropylbetaine, fatty acid alkanolamide or monoalkyl glyceryl ether in combination with Component (A) is desired because combined use of them not only improves the foaming power but also gives the agent with adequate liquid properties.

The content of the nonionic or amphoteric surfactant in the aqueous hair cleansing agent of the present invention is preferably from 0.1 to 15 weight %, because it is effective for desirably increasing the foam volume. From this viewpoint, it is more preferably from 0.5 to 8 weight %, even more preferably from 1 to 6 weight %.

Furthermore, the aqueous hair cleansing agent of the present invention may contain a cationic surfactant, a cationized polymer other than Component (B) and a silicone other than Component (C) in order to improve the finish after drying.

Examples of the cationic surfactant include alkyltrimethylammonium salts, alkoxytrimethylammonium salts, dialkyldimethylammonium salts, alkyldimethylamines and salts thereof, alkoxydimethylamines and salts thereof, and alkylamidodimethylamines and salts thereof.

(i) As the alkyltrimethylammonium salts, those represented by the following formula can be used:

wherein, $R^{13}$ represents a $C_{12-22}$ alkyl group, and $X^-$ represents a halide ion such as chloride ion or bromide ion.

Specific examples include cetyltrimethylammonium chloride, stearyltrimethylammonium chloride and behenyltrimethylammonium chloride.

(ii) As the alkoxytrimethylammonium salts, those represented by the following formula can be used:

$$R^{14}-O-R^{15}-N^+(CH_3)_3 X^-$$

wherein, $R^{14}$ represents a $C_{12-22}$ alkyl group, $R^{15}$ represents an ethylene or propylene group which may be substituted with a hydroxy group, and $X^-$ has the same meaning as described above.

Specific examples include stearoxypropyltrimethylammonium chloride, stearoxyethyltrimethylammonium chloride and stearoxyhydroxypropyltrimethylammonium chloride.

(iii) As the dialkyldimethylammonium salts, those represented by the following formula can be used:

$$(R^{16})_2 N^+ (CH_3)_2 X^-$$

wherein, $R^{16}$ each independently represents a $C_{12-22}$ alkyl group or a benzyl group, and $X^-$ has the same meaning as described above.

Specific examples include distearyldimethylammonium chloride.

(iv) As the alkyldimethylamines and salts thereof, those represented by the following formula can be used:

$$R^{17}-N(CH_3)_2$$

wherein, $R^{17}$ represents a $C_{12-22}$ alkyl group.

Specific examples include behenyldimethylamine and stearyldimethylamine, and organic acid salts thereof.

(v) As the alkoxydimethylamines and salts thereof, those represented by the following formula and salts thereof can be used:

$$R^{18}-O-R^{19}-N(CH_3)_2$$

wherein, $R^{18}$ represents a $C_{12-22}$ alkyl group, and $R^{19}$ represents an ethylene or propylene group.

(vi) As the alkylamidodimethylamines and salts thereof, those represented by the following formula and salts thereof can be used:

$$R^{20}-C(=O)NH-R^{21}-N(CH_3)_2$$

wherein, $R^{20}$ represents a $C_{11-21}$ alkyl group, and $R^{21}$ represents an ethylene or propylene group.

Examples of the cationic surfactant other than those described in (i) to (vi) include lanolin fatty acid aminopropylethyldimethylammonium ethyl sulfate, lanolin fatty acid aminoethyltriethylammonium ethyl sulfate, lanolin fatty acid aminopropyltriethylammonium ethyl sulfate, lanolin fatty acid aminoethyltrimethylammonium methyl sulfate, lanolin fatty acid aminopropylethyldimethylammonium methyl sulfate, isoalkanoic acid $(C_{14}-C_{20})$aminopropylethyldimethylammonium ethyl sulfate, isoalkanoic acid $(C_{18}-C_{22})$aminopropylethyldimethylammonium ethyl sulfate, isostearic acid aminopropylethyldimethylammonium ethyl sulfate, isononanoic acid aminopropylethyldimethylammonium ethyl sulfate, and alkyltrimethylammonium saccharins.

These cationic surfactants may be used in combination of two or more. The content thereof in the aqueous hair cleansing agent of the present invention is preferably from 0.01 to 10 weight %, more preferably from 0.05 to 6 weight %, even more preferably from 0.3 to 3 weight %, even more preferably from 0.5 to 2 weight % from the viewpoint of smoothness during shampooing and rinsing.

Examples of the cationized polymer other than Component (B) include cationized cellulose, cationized starch, cationized guar gum, cationized locust bean gum, diallyldialkylammonium salt/acrylamide copolymers, vinylimidazolium chloride/vinylpyrrolidone copolymers, hydroxyethyl cellulose/dimethyldiallylammonium chloride copolymers, vinylpyrrolidone/quaternized dimethylaminoethyl methacrylate copolymers, vinylpyrrolidone/alkylamino acrylate copolymers, vinylpyrrolidone/alkylamino acrylate/vinylcaprolactam copolymers, vinylpyrrolidone/methacrylamidopropyl trimethylammonium chloride copolymers, alkylacrylamide/alkyl acrylate/alkylaminoalkylacrylamide/polyethylene glycol methacrylate copolymers, adipic acid/dimethylaminohydroxypropylethylenetriamine copolymer ("Cartaretin", product of Sandoz/USA), and cationic polymers as described in JP-A-53-139734 and JP-A-60-36407. Of these, cationized cellulose and cationized guar gum, and diallyldialkylammonium salt/acrylamide copolymers are preferred.

Usable are, for example, commercially available products such as "Merquat 550" (copolymer of acrylamide and diallyldimethylammonium salt; CTFA name: Polyquaternium-7; product of ONDEO-NALCO), "Luviquat FC370" (copolymer of 1-vinyl-2-pyrrolidone and 1-vinyl-3-methylimidazolium salt; CTFA name: polyquaternium-16; product of BASF), "Gafquat 755N" (copolymer of 1-vinyl-2-pyrrolidone and dimethylaminoethyl methacrylate; CTFA name: polyquaternium-11; product of ISP), "Ucare Polymer JR series" and "Ucare Polymer LR series" (salt of a reaction product of trimethylammonium substituted epoxide with hydroxyethyl cellulose; CTFA name: polyquaternium-10; product of Amerchol), "Poiz C-60H", "Poiz C-80M" and "Poiz C-150L" (salt of a reaction product of trimethylammonium substituted epoxide with hydroxyethyl cellulose; CTFA name; polyquaternium-10; product of Kao); "Jaguar series" (guar hydroxypropyltrimethylammonium chloride; product of Rhodia); and "Catinal CLB-100" (locust bean hydroxypropyltrimonium chloride, product of Toho Chemical Industry).

These cationized polymers other than Component (B) may be used in combination of two or more. From the viewpoint of the smoothness during shampooing and rinsing, the content thereof in the aqueous hair cleansing agent of the present invention preferably ranges from 0.01 to 3 weight %, more preferably from 0.05 to 2 weight %, even more preferably from 0.1 to 0.5 weight %.

The aqueous hair cleansing agent of the present invention preferably contains, as Component (E), a dimethylpolysiloxane represented by the following formula:

$$R^{23}(CH_3)_2 SiO-[(CH_3)_2 SiO]_k-Si(CH_3)_2 R^{23}$$

wherein, $R^{23}$ represents a methyl or hydroxyl group and k stands for a number from 1 to 20,000.

The dimethylpolysiloxane (silicone oil) is dispersed in the aqueous hair cleansing agent of the present invention. The average particle size of the dispersed particles of a dimethylpolysiloxane is preferably less than 100 μm, more preferably 50 μm or less, even more preferably 4 μm or less, even more preferably 2 μm or less. The average particle size is preferably 0.1 μm or greater in view of the feeling upon use and conditioning effects.

As such a dimethylpolysiloxane, usable are, for example, "Silicone CF2450" of Dow Corning Toray containing 60 weight % of a dimethylpolysiloxane oil of the above-described formula in which k stands for 300 to 6500 and having an average particle size of 0.8 μm and "Silicone CF2460" containing 50 weight % of a dimethylpolysiloxane oil of the above formula in which k stands for 300 to 6,500 and having an average particle size of 20 μm.

In addition, silicones other than Components (C) and (E) may be incorporated. Examples of such silicones include amino-modified silicones other than Component (C), polyether-modified silicones, methylphenylpolysiloxane, fatty acid-modified silicones, alcohol-modified silicones, alkoxy-modified silicones, epoxy-modified silicones, fluorine-modified silicones, cyclic silicone and alkyl-modified silicones.

Two or more of these silicones other than Components (C) and (E) may be used in combination. The content thereof in the aqueous hair cleansing agent of the present invention is preferably from 0.01 to 10 weight %, more preferably from 0.05 to 5 weight %, even more preferably from 0.1 to 2 weight % from the viewpoint of the smoothness during shampooing and rinsing.

The aqueous hair cleansing agent of the present invention may further contain, as a pearling agent, an ethylene glycol monofatty acid ester, ethylene glycol difatty acid ester, ethylene glycol monoalkyl ether or ethylene glycol dialkyl ether.

Examples of the ethylene glycol monofatty acid ester include ethylene glycol monostearate and ethylene glycol monobehenate; and those of the ethylene glycol difatty acid ester include ethylene glycol distearate and ethylene glycol dibehenate. Examples of the ethylene glycol monoalkyl ether include ethylene glycol monostearyl ether, while those of the ethylene glycol dialkyl ether include ethylene glycol distearyl ether.

Two or more of these pearling agents may be used in combination and the content thereof in the aqueous hair cleansing agent of the present invention is preferably from 0.1 to 10 weight %, more preferably from 0.5 to 5 weight %, even more preferably from 1 to 4 weight % in order to improve the storage stability of the aqueous hair cleansing agent and improving its smoothness during foaming and rinsing.

The aqueous hair cleansing agent of the present invention may contain an oil as another conditioning agent. Examples of the oil include hydrocarbons such as squalene, squalane, liquid paraffin, liquid isoparaffin, and cycloparaffin; oils or fats such as castor oil, cacao oil, mink oil, avocado oil, olive oil, sunflower oil and camellia oil; waxes such as beeswax, spermaceti, lanolin, and carnauba wax; higher alcohols such as cetyl alcohol, oleyl alcohol, stearyl alcohol, isostearyl alcohol, 2-octyldodecanol, myristyl alcohol, behenyl alcohol and cetostearyl alcohol; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate and tridecyl isononanoate; higher fatty acids such as capric acid, lauric acid, myristic acid, palmitic acid, stearic acid, behenic acid, oleic acid, coconut oil fatty acid, isostearic acid, and isopalmitic acid; and other oils such as isostearyl glyceryl ether and polyoxypropylene butyl ether. Of these, higher alcohols and oils or fats are preferred, with myristyl alcohol, cetyl alcohol, stearyl alcohol, sunflower oil and camellia oil are more preferred. These oils may be use either singly or in combination of two or more. The content thereof in the aqueous hair cleansing agent of the present invention is preferably from 0.1 to 2 weight %, more preferably from 0.2 to 1.5 weight %, even more preferably from 0.3 to 1 weight %.

The aqueous hair cleansing agent of the present invention may contain a viscosity regulator. Examples of the viscosity regulator include hydroxyethyl cellulose, methyl cellulose, polyethylene glycol, polypropylene glycol, ethylene glycol, propylene glycol, isoprene glycol, ethanol, benzyl alcohol, benzyl oxyethanol, phenoxyethanol, clay minerals, and salts such as sodium chloride, ammonium chloride, sodium citrate and the like. Of these, benzyl alcohol, ethanol, polypropylene glycol, sodium chloride and sodium citrate are preferred. Two or more of these viscosity regulators may be used in combination. The amount used thereof in the aqueous hair cleansing agent of the present invention is preferably from 0.01 to 5 weight %, more preferably from 0.05 to 4 weight %, even more preferably from 0.1 to 3 weight % from the standpoints of the volume and quality of foam.

In addition to the above-described components, components which are employed in ordinary aqueous hair cleansing agents can be incorporated in the aqueous hair cleansing agent of the present invention as needed depending on the purpose of use. Such components include, for example, anti-dandruff agents; vitamin preparations; bactericides; anti-inflammatories; antiseptics; chelating agents; humectants such as glycerin, sorbitol and panthenol; colorants such as dyes and pigments; extracts such as extracts of eucalyptus in a polar solvent, proteins available from shells having a pearl layer or pearls or hydrolysates thereof, honey, royal jelly, proteins available from silk or hydrolysates thereof, protein-containing extracts available from seeds of leguminous plants, Asian ginseng extract, rice bran extract, *Fucus vesiculosus* extract, aloe extract, Alpinia Leaf extract, and chlorella extract; pearling agents such as titanium oxide; perfumes; ultraviolet absorbers; antioxidants; and other components listed in ENCYCLOPEDIA OF SHAMPOO INGREDIENTS (MICELLE PRESS).

The aqueous hair cleansing agent of the present invention has preferably a pH (25° C., diluted 20-fold with water) of from 2 to 6, more preferably from 3 to 5, even more preferably from 3.5 to 4.5 when it is applied to the hair, from the viewpoint of improving the luster and manageability of the hair. As a pH regulator, organic acids are preferred, with α-hydroxy acids being more preferred. Specific preferred examples include malic acid, citric acid, lactic acid and glycolic acid. As the pH regulator, two or more of these organic acids may be used in combination. The amount used thereof is preferably from 0.01 to 5 weight %, more preferably from 0.1 to 3 weight %, even more preferably from 0.3 to 2 weight % in the aqueous hair cleansing agent of the present invention from the viewpoints of improvement in foam quality and flexibility of hair during shampooing. As another pH regulator, a base such as sodium hydroxide, potassium hydroxide or ammonium chloride may be used in combination with the above-described organic acid.

Although the form of the aqueous hair cleansing agent of the present invention can be chosen as desired from a liquid form, a gel form and the like, a liquid form in a solvent such as water or a lower alcohol is preferred, with water being more preferred.

The following examples further describe and demonstrate embodiments of the present invention. The examples are given solely for the purpose of illustration and are not to be construed as limitations of the present invention.

EXAMPLES

Examples 1 to 4 and Comparative Examples 1 to 4

Hair cleansing agents shown in Table 1 were prepared and they were evaluated by the below-described evaluation method. The results are also shown in Table 1. The pH is a value of the agent measured at 25° C. after it is diluted 20-fold with water.

(1) Foaming Speed

Figure 1:
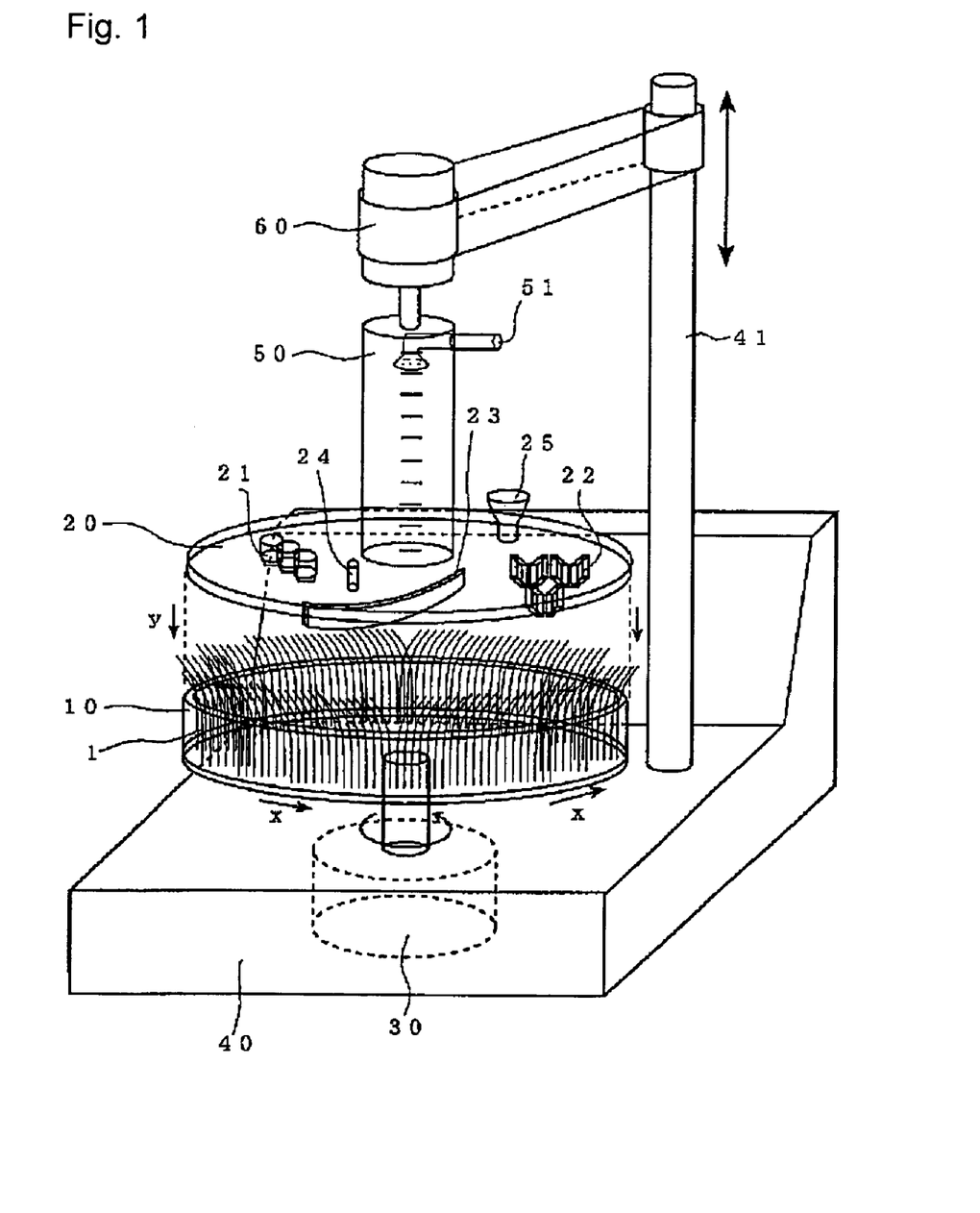
FIG. 1 is an overall view of an apparatus employed for the evaluation of foaming speed.

The foaming speed was measured using an apparatus shown in FIG. 1.

Figure 2:
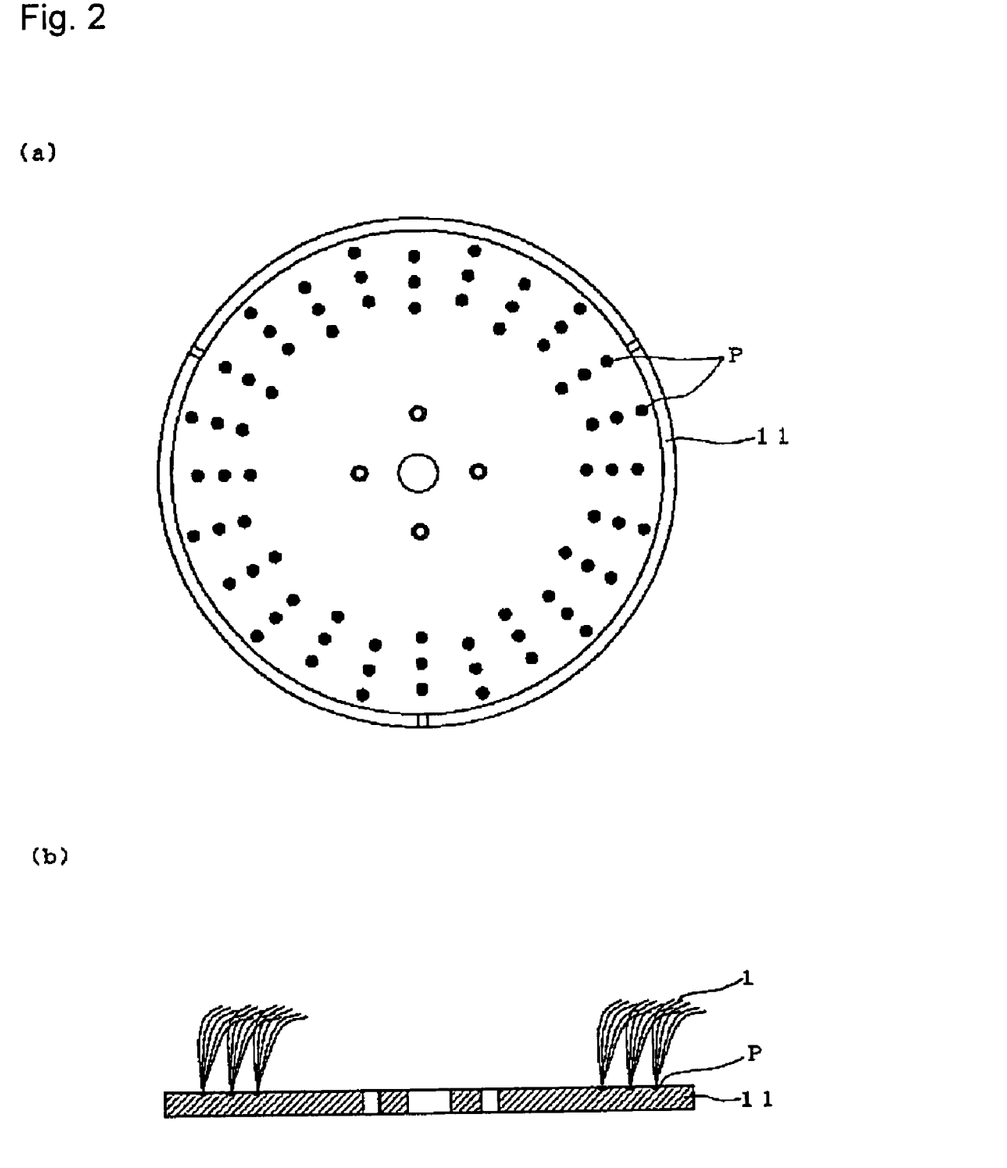

The apparatus of FIG. 1 is equipped with an open-topped cylindrical container 10 (diameter: 160 mm, height: 55 mm) made of transparent plastic and having a drain outlet (not illustrated) at the bottom of the container, a lid 20 made of transparent plastic, a control unit 40 having a motor 30 loaded therein, a metering instrument 50 and a torque detector 60. A disk 11 (diameter: about 160 mm) having a plurality of implant holes P into which hairs 1 (90 mm, 30 g in total) have been implanted as illustrated in FIG. 2 is installed inside the container 10. The container 10 is rotated in the direction of an arrow x by the motor 30, whereby the hairs 1 in the container 10 are also rotated.

The lid 20 has, on the back side thereof, first protrusions 21 (3 cylindrical protrusions each having a diameter of 15 mm and height of 12 mm) corresponding to human fingers and second protrusions 22 (9 protrusions each having length of 10 mm, width of 2 mm and height of 12 mm) corresponding to a brush. The lid 20 is brought into contact with the hairs 1 when the lid 20 is put on the upper surface of the container 10 in the direction of an arrow y. The lid 20 has a funnel-like inlet 25 for pouring a cleansing agent therefrom. When the lid 20 is put on the container 10, it is not fixed to the container 10 but is supported by a support 41 via the torque detector 60 and metering instrument 50. Accordingly, rotation of the container 10 with the lid 20 thereon causes a sliding contact of the hairs 1 in the container 10 with the protrusions 21 and 22. When the cleansing agent is poured onto the hairs 1 from the inlet 25, the cleansing agent can therefore be foamed as if the hairs are actually shampooed.

First, the hairs were wetted with 30 g of water and 0.3 mL of a model sebum made of lanolin was added. Then, 1.5 mL of a sample to be evaluated was poured. The container 10 was then rotated at a speed of 70 revolutions per minute to cause a sliding contact between the hairs 1 and the protrusions 21 and 22. Foams thus generated were collected in the metering instrument 50 and the cleansing agent was evaluated based on the time until the foam volume reached 25 mL in accordance with the below-described criteria.

A: less than 100 seconds
B: 100 seconds or greater but less than 200 seconds
C: 200 seconds or greater but less than 300 seconds
D: 300 seconds or greater (2) Smoothness During Foaming After a human hair tress of 25 cm in length, 5.5 cm in width and 10 g in weight was rinsed lightly with hot water of 40° C., excess water was removed. 0.5 g of a hair cleansing agent was applied thereon to foam sufficiently for about 30 seconds. The smoothness was organoleptically evaluated during the foaming. Evaluation was carried out by a panel of five experts and their total scores were indicated. Criteria for evaluation are as follows:

4: Very smooth
3: Smooth
2: Not so smooth
1: Not smooth (3) Smoothness During Rinsing After a human hair tress of 25 cm in length, 5.5 cm in width and 10 g in weight was rinsed lightly with hot water of 40° C., excess water was removed. 0.5 g of a hair cleansing agent was applied thereon to foam sufficiently for about 30 seconds. The smoothness was organoleptically evaluated while rinsing the lathered hair tress with hot water of 40° C. having a flow rate of 2 L/min. Evaluation was carried out by a panel of five experts and their total scores were indicated. Criteria for evaluation are as follows:

4: Very smooth
3: Smooth
2: Not so smooth
1: Not smooth (4) Luster and Manageability after Drying A hair tress treated in a similar manner as the evaluation of smoothness was rinsed with running water (2 L/min) of 40° C. and then towel-dried sufficiently. After natural drying, the luster and manageability were evaluated visually. They were evaluated by a panel of 5 experts and total scores were indicated. Criteria for evaluation are as described below:

4: Very good
3: Good
2: Not so good
1: Not good (5) Stability

The hair cleansing agent (100 mL) was filled in a 110-mL capped bottle and after storage at 50° C. for 1 month, it was evaluated in accordance with the following evaluation criteria.

A: No change is observed after storage.
B: A slight change is observed after storage (within an allowance)
C: An apparent change is observed after storage (outside an allowance)

TABLE 1

| | | Examples | | | | Comparative Examples | | | |
|---|---|---|---|---|---|---|---|---|---|
| | (weight %) | 1 | 2 | 3 | 4 | 1 | 2 | 3 | 4 |
| Component (A) | Ammonium lauryl ether (1) sulfate*[1] | 12 | 12 | 12 | 12 | 12 | 12 | 12 | 12 |
| Component (B) | Cationized tara gum*[2] | 0.5 | 0.5 | 0.5 | 0.5 | 0.5 | 0.5 | — | — |
| Comparative Component (B') | Cationized hydroxyethyl cellulose*[3] | — | — | — | — | — | — | 0.5 | — |
| | Cationized guar gum*[4] | — | — | — | — | — | — | — | 0.5 |
| Component (C) | Amino-modified silicone*[5] | 0.5 | 1.0 | — | — | — | — | 0.5 | — |
| | Amino-modified silicone*[6] | — | — | 0.5 | 0.1 | — | — | — | 0.5 |
| Comparative Component (C') | Amino-modified silicone*[7] | — | — | — | — | 0.5 | — | — | — |
| Other components | Ethylene glycol distearate | 2 | 2 | 2 | 2 | 2 | 2 | 2 | 2 |
| | Lauroylamidopropylbetaine | 1.5 | 1.5 | 1.5 | 1.5 | 1.5 | 1.5 | 1.5 | 1.5 |
| | Myristyl alcohol | 1 | 1 | 1 | 1 | 1 | 1 | 1 | 1 |
| | Cocoyl monoethanolamide | 0.5 | 0.5 | 0.5 | 0.5 | 0.5 | 0.5 | 0.5 | 0.5 |
| | Isodecyl glyceryl ether*[8] | 0.5 | 1.0 | 1.0 | 1.0 | 0.2 | — | 0.5 | 0.5 |
| | Dimethicone*[9] | 1 | 1 | 1 | 1 | 1 | 1 | 1 | 1 |
| | Benzyl alcohol | 0.5 | 0.5 | 0.5 | 0.5 | 0.5 | 0.5 | 0.5 | 0.5 |

TABLE 1-continued

|  | (weight %) | Examples 1 | Examples 2 | Examples 3 | Examples 4 | Comparative Examples 1 | Comparative Examples 2 | Comparative Examples 3 | Comparative Examples 4 |
|---|---|---|---|---|---|---|---|---|---|
|  | Sodium chloride | 0.2 | 0.2 | 0.2 | 0.2 | 0.2 | 0.2 | 0.2 | 0.2 |
|  | Malic acid | 0.7 | 0.7 | 0.7 | 0.7 | 0.7 | 0.7 | 0.7 | 0.7 |
|  | Purified water | Balance | Balance | Balance | Balance | Balance | Balance | Balance | Balance |
|  | Total | 100 | 100 | 100 | 100 | 100 | 100 | 100 | 100 |
|  | pH | 3.9 | 3.9 | 3.9 | 3.9 | 3.9 | 3.9 | 3.9 | 3.9 |
| Evaluation | Foaming speed | A | B | A | A | B | D | C | C |
|  | Smoothness during foaming | 19 | 19 | 18 | 17 | 17 | 10 | 13 | 14 |
|  | Smoothness during rinsing | 19 | 18 | 20 | 17 | 10 | 14 | 12 | 14 |
|  | Luster and manageability after drying | 19 | 20 | 18 | 14 | 9 | 14 | 15 | 13 |
|  | Stability | A | A | A | A | C | A | B | A |

*[1]Ammonium polyoxyethylene (1) lauryl ether sulfate; the average number of moles of ethylene oxide: 1
*[2]Cationized tara gum: "Catinal CTR-100" (product of Toho Chemical Industry)
*[3]Cationized hydroxyethyl cellulose; "Poiz C-80M" (product of Kao)
*[4]Cationized guar gum; "Jaquar C-13S" (product of Rhodia)
*[5]Amino-modified silicone: "8500 Conditioning Agent" (product of Dow Corning Toray)
*[6]Amino-modified silicone: "DOW CORNING TORAY SS-3588" (product of Dow Corning Toray)
*[7]Amino-modified silicone: "Silicone KT-1989" (product of GE Toshiba Silicone)
*[8]Isodecyl glyceryl ether: which is derived from an alcohol obtained by the conversion of a trimer of propylene by the oxo process (which will equally apply hereinafter)
*[9]Dimethylpolysiloxane emulsion: viscosity (10000 mm$^2$/s)/(10 mm$^2$/s) = 95/5 mixture, an average particle size: 4.0 μm, a dimethylpolysiloxane content: 60 weight %.

Example 5

Conditioning Shampoo

| | (weight %) |
|---|---|
| Ammonium polyoxyethylene (1) lauryl ether sulfate (average number of moles of ethylene oxide: 1) | 13.0 |
| Cationized tara gum ("Catinal "CTR-100", product of Toho Chemical Industry) | 0.2 |
| Amino-modified silicone ("8500 Conditioning Agent", Product of Dow Corning Toray) | 0.3 |
| Cationized cellulose ("Poiz C-80M", product of Kao) | 0.3 |
| Diallyldimethylammonium chloride/acrylamide copolymer ("Merquat 550", product of Ondeo Nalco, effective content: 8.5 weight %) | 1.7 |
| Dimethylpolysiloxane emulsion (silicone viscosity: 10,000 mm$^2$/s, average particle size: 4 μm, effective content: 60 weight %) | 1.7 |
| Ethylene glycol distearate | 2.0 |
| Isodecyl glyceryl ether | 0.5 |
| Lauroyl amidopropylbetaine | 1.0 |
| Myristyl alcohol | 0.4 |
| Cetyl alcohol | 0.1 |
| Cocoyl monoethanolamide | 0.5 |
| Polyoxyethylene (16) lauryl ether | 0.7 |
| Polypropylene glycol (weight average molecular weight: 400) | 0.5 |
| Benzyl alcohol | 0.3 |
| Ethanol | 3.0 |
| Camellia oil | 0.01 |
| Panthenol | 0.05 |
| Royal jelly | 0.01 |
| Purified honey | 0.01 |
| Silk extract | 0.05 |
| Sodium chloride | 0.2 |
| Perfume | q.s. |
| Malic acid | 0.5 |
| pH regulator (lactic acid) | An amount to adjust pH to 3.9 |
| Ion exchange water | Balance |

Example 6

Conditioning Shampoo

| | (weight %) |
|---|---|
| Sodium polyoxyethylene (2) lauryl ether sulfate (average number of moles of ethylene oxide: 2) | 13.0 |
| Cationized tara gum ("Catinal CTR-200", product of Toho Chemical Industry) | 0.5 |
| Amino-modified silicone ("SS-3588", product of Dow Corning Toray) | 0.1 |
| Cationized guar gum ("Jaguar C-17", product of Rhodia) | 0.1 |
| Diallyldimethylammonium chloride homopolymer ("Merquat 100", product of Ondeo Nalco, effective content: 40 weight %) | 0.8 |
| Highly polymerized dimethylpolysiloxane emulsion ("Silicone CF2450", product of Dow Corning Toray, particle size: 0.2 to 0.8 μm, effective content: 60 weight %) | 2.0 |
| Ethylene glycol distearate | 3.0 |
| Isodecyl glyceryl ether | 0.7 |
| Lauroyl amidopropylbetaine | 2.0 |
| Cocoyl monoethanolamide | 0.5 |
| Myristyl alcohol | 0.5 |
| Cetyl alcohol | 0.5 |
| Polyoxyethylene (16) lauryl ether | 1.0 |
| Benzyl alcohol | 1.0 |
| Propylene glycol (weight average molecular weight: 400) | 0.2 |
| Sodium chloride | 1.0 |
| Hydrolyzed conchiolin solution (dry content: 3 weight %) | 0.05 |
| Asian ginseng extract (dry content: 3 weight %) | 0.05 |
| Soybean extract (dry content: 0.4 weight %) | 0.05 |
| Eucalyptus extract (dry content: 0.2 weight %) | 0.05 |
| Rice bran oil | 0.05 |
| Glycolic acid | 1.0 |
| Perfume | q.s. |
| pH regulator (sodium hydroxide) | Amount to adjust pH to 3.9 |
| Ion exchange water | Balance |

Example 7

Conditioning Shampoo

|  | (weight %) |
|---|---|
| Sodium polyoxyethylene (1) lauryl ether sulfate (average number of moles of ethylene oxide: 1) | 16.0 |
| Cationized tara gum ("Catinal "CTR-100", product of Toho Chemical Industry) | 0.7 |
| Amino-modified silicone ("8500 Conditioning agent", Product of Dow Corning Toray) | 0.5 |
| Highly polymerized dimethylpolysiloxane emulsion ("Silicone CF2460", product of Dow Corning Toray, particle size: 20 μm, effective content: 75 weight %) | 3.0 |
| Ethylene glycol distearate | 3.0 |
| 2-Ethylhexyl glyceryl ether | 0.3 |
| Cocoyl monoethanolamide | 0.5 |
| Stearyl alcohol | 1.0 |
| Glycerin | 1.0 |
| Sodium chloride | 0.2 |
| Benzyloxyethanol | 0.5 |
| Malic acid | 0.7 |
| Perfume | q.s. |
| Lactic acid | 0.1 |
| pH regulator (citric acid) | Amount to adjust pH to 5.5 |
| Ion exchange water | Balance |

Example 8

Conditioning Shampoo

|  | (weight %) |
|---|---|
| Sodium polyoxyethylene (2.5) lauryl ether sulfate (average number of moles of ethylene oxide: 2.5) | 15.0 |
| Cationized tara gum ("Catinal CTR-200", product of Toho Chemical Industry) | 0.2 |
| Amino-modified silicone ("SILSTYLE 104", product of Dow Corning Toray) | 1.0 |
| Cationized locust bean gum ("Catinal CLB-100", Product of Toho Chemical Industry) | 0.2 |
| Methylpolysiloxane emulsion (silicone viscosity: 5,000 mm²/s, particle size: 0.2 to 0.8 μm, effective content: 65 weight %) | 2.0 |
| Ethylene glycol distearate | 2.0 |
| Lauroyl amidopropylbetaine | 3.0 |
| Cocoyl monoethanolamide | 0.8 |
| Polyoxyethylene (16) lauryl ether | 2.0 |
| Sodium Cocoamphoacetate | 1.0 |
| Stearoxypropyl dimethylamine•malate salt | 0.5 |
| Polypropylene glycol (weight average molecular weight: 400) | 0.5 |
| Sodium chloride | 1.0 |
| Malic acid | 0.8 |
| Citric acid | 0.75 |
| pH regulator (sodium hydroxide) | Amount to adjust pH to 3.5 |
| Ion exchange water | Balance |

Hair cleansing agents obtained in Examples 5 to 8 lathered quickly, were excellent in the smoothness of the hair during foaming and rinsing, provided excellent luster and manageability to the finished hair, and had excellent storage stability.

The invention claimed is:

1. An aqueous hair cleansing agent comprising components (A), (B) and (C):

(A) an anionic surfactant represented by the formula (5) or (6):

$$R^9O(CH_2CH_2O)_mSO_3M \quad (5)$$

$$R^9OSO_3M \quad (6)$$

wherein, $R^9$ represents a C10-18 alkyl or alkenyl group, M represents an alkali metal, alkaline earth metal, ammonium, or a cation derived from alkanolamine or basic amino acid, and m stands for an average number by weight of from 1 to 5;

(B) a galactomannan polysaccharide consisting of a cationized tara gum; and (C) an amino-modified silicone represented by formula (1) or (4):

wherein, $R^1$ each independently represents a monovalent hydrocarbon group, a hydroxy group or an alkoxy group,

$R^2$ each independently represents a monovalent hydrocarbon group, $R^3$ represents a divalent $C_{1-10}$ hydrocarbon group, $R^4$ represents a group represented by the formula (2) or (3):

wherein Y represents a hydrogen atom or a group —$CH_2$—$CH(OH)$—$R^3$—OH, $R^3$ has the same meaning as defined above, $R^5$ represents a hydrogen atom or a group —$R^3NY_2$, Y and $R^3$ have the same meanings as defined, above, with the proviso that all the Ys do not represent a hydrogen atom at the same time, a in the formula (1) stands for a number from 25 to 1000, and b stands for a number from 1 to 200;

wherein, $R^6$ each independently represents a hydrogen atom or a monovalent $C_{1-6}$ hydrocarbon group, $R^7$ represents either $R^6$ or E, E represents a group represented by —$R^8$—Z, wherein $R^8$ represents a direct bond or a divalent $C_{1-20}$ hydrocarbon group, and Z represents a primary, secondary or tertiary amino-containing group or ammonium-containing group, X represents a divalent group, c stands for a number of 2 or greater, d stands for a number of 1 or greater, n stands for a number from 2 to 10, e stands for a number of 4 or greater and stands for a number of 2 or greater.

2. The aqueous hair cleansing agent according to claim 1, comprising from 1 to 30 weight % of Component (A), from 0.01 to 10 weight % of Component (B) and from 0.01 to 10 weight % of Component (C).

3. The aqueous hair cleansing agent according to claim 1, wherein a ratio by weight of Components (B)/(C) falls within a range of from 1/10 to 10/1.

4. The aqueous hair cleansing agent according to claim 1, which further comprises, as Component (D), a glyceryl ether selected from the group consisting of a monoalkyl glyceryl ether having a $C_{4-10}$ alkyl group and a monoalkenyl glyceryl ether having a $C_{4-10}$ alkenyl group.

5. The aqueous hair cleansing agent according to claim 1, further comprising dimethylpolysiloxane as Component (E).

6. The aqueous hair cleansing agent according to claim 1, which has a pH of from 2 to 6 at 25° C. when diluted 20-fold with water.

7. The aqueous hair cleansing agent according to claim 1, wherein (A) the anionic surfactant is ammonium lauryl ether sulfate.

8. The aqueous hair cleansing agent according to claim 1, wherein (A) the anionic surfactant is present in an amount of 8 to 20 weight %.

9. The aqueous hair cleansing agent according to claim 1, wherein (B) the cationized tara gum is present in an amount of 0.03 to 2 weight %.

10. The aqueous hair cleansing agent according to claim 1, wherein (C) the amino-modified silicone is present in an amount of 0.03 to 2 weight %.

11. The aqueous hair cleansing agent according to claim 1, wherein (C) the amino-modified silicone is represented by formula (4).

12. The aqueous hair cleansing agent according to claim 1, wherein (C) the amino-modified silicone is represented by formula (1).

13. The aqueous hair cleansing agent according to claim 1, wherein $R^4$ of formula (1) of component (C) represents a group of formula (3).

* * * * *